United States Patent [19]

Johnson

[11] Patent Number: 4,721,617

[45] Date of Patent: Jan. 26, 1988

[54] VACCINE AGAINST LYME DISEASE

[75] Inventor: Russell C. Johnson, St. Paul, Minn.

[73] Assignee: Regents of the University of Minnesota, Minneapolis, Minn.

[21] Appl. No.: 896,665

[22] Filed: Aug. 14, 1986

[51] Int. Cl.$^4$ .............................................. A61K 39/02
[52] U.S. Cl. ...................................... 424/92; 424/88; 435/240
[58] Field of Search ...................... 424/92, 88; 435/240

[56] References Cited

U.S. PATENT DOCUMENTS

| | | | |
|---|---|---|---|
| Re. 31,672 | 9/1969 | Kasper | 536/53 |
| 3,470,294 | 9/1986 | Drager et al. | 424/89 |
| 4,367,223 | 1/1983 | Kasper | 424/92 |
| 4,447,537 | 5/1984 | Yunker et al. | 424/89 X |
| 4,469,672 | 9/1984 | Harris | 424/23 |
| 4,514,498 | 4/1985 | Kettman et al. | 435/240 |
| 4,596,707 | 6/1986 | Ristic et al. | 424/85 X |

OTHER PUBLICATIONS

Nature, 280, Aug. 1979, 491–493, Allen et al.
*Lyme Disease*, pub. by Pfizer Central Research (1986).
Steere et al., N. Engl. J. Med., 1983; 308: 733–40.
Barbour, A. G., Yale J. Biol. Med., 1984: 57: 521–525.
Johnson et al., 2nd International Symp. on Lyme Disease and Related Disorders, Sep. 17–19, 1985, abstract.

*Primary Examiner*—Howard E. Schain
*Attorney, Agent, or Firm*—Merchant, Gould, Smith, Edell, Welter & Schmidt

[57] ABSTRACT

A vaccine for the immunization of mammals against Lyme borreliosis (Lyme disease) is disclosed which contains an effective amount of inactivated *Borrelia burgdorferi* spirochetes dispersed in a physiologically-acceptable, non-toxic liquid vehicle.

6 Claims, No Drawings

VACCINE AGAINST LYME DISEASE

This invention was made with Government support under Public Health Service Grant AM 34733. The Government has certain rights in this invention.

BACKGROUND OF THE INVENTION

Lyme borreliosis (Lyme disease and related disorders) is a zoonosis characterized by a number of variable syndromes. The etiological agent of this disease is the spirochete *Borrelia burgdorferi*, which is primarily transmitted by Ixodes ticks. The northern deer tick, *Ixodes dammini* is the major vector of Lyme disease in Minnesota, Wisconsin, the northeastern United States and adjacent Canada. The California black-legged tick, *I. pacificus* is the primary vector of this disease in the western United States, and in Europe the major vector of Lyme borreliosis is *I. ricinus*. The spirochete has also been found in deerflies, horseflies and mosquitos. The preferred hosts for the larval and nymphal stages of these ticks are small rodents such as *Peromyscus leucopus*, the white-footed mouse, whereas the adult ticks preferentially feed on large mammals, such as deer. Since transovarial transmission of the spirochetes by these ticks occurs infrequently, the disease is transmitted by the nymphal and adult ticks. The frequent isolation of *B. burgdorferi* from white-footed mice captured in foci of Lyme disease suggests that small rodents may serve as a natural reservoir for this spirochete and source of infection for the larval and/or nymphal stages of the tick. Local spread of the Ixodes ticks is by mammalian hosts, and birds may serve an important role in long distance tick dispersal.

Most cases of Lyme disease occur in June or July, when the aggressive nymphal stage is most active. As many as two-thirds of the people that become infected by this spirochete are unaware of the tick bite because of the painless bite and the small size (several mm) of the nymphal stage.

Spirochetes are introduced into the host at the site of the tick bite and this is also the location of the initial characteristic skin lesion, erythema chronicum migrans (ECM). A systemic illness ensues due to the lymphatic and hematogenous spread of *B. burgdorferi*. The early phase of the illness often consists of the ECM, headache, fatigue, muscle and joint aches, stiff neck and chills and fever. This phase of the disease may be followed by neurologic, joint or cardiac abnormalities. The chronic forms of the disease such as arthritis (joint involvement), acrodermatitis chronica atrophicans (skin involvement), and Bannwart's syndrome (neurological involvement) may last for months to years and are associated with the persistence of the spirochete. A case of maternal-fetal transmission of *B. burgdorferi* resulting in neonatal death has been reported. Domestic animals such as the dog also develop arthritis and lameness to this tick-borne infection. For every symptomatic infection, there is at least one asymptomatic infection. Lyme disease is presently the most commonly reported tick-borne disease in the United States.

The infection may be treated at any time with antibiotics such as penicillin, erythromycin, tetracycline, and ceftriaxone. Once infection has occurred, however, the drugs may not purge the host of the spirochete but may only act to control the chronic forms of the disease. Complications such as arthritis and fatigue may continue for several years after diagnosis and treatment.

Since the effectiveness of the present methods of treatment are limited, and vector control is impractical at best, a need exists for a vaccine which is effective to immunize high-risk individuals and susceptible domestic animals against Lyme borreliosis.

SUMMARY OF THE INVENTION

The present invention is directed to a vaccine which is effective to immunize susceptible mammals, such as domestic animals and humans, against Lyme borreliosis. The vaccine comprises an effective amount of inactivated *Borrelia burgdorferi* spirochetes which can be derived from vectors or infected hosts. The immunogenic spirochetes are suspended in a physiologically-acceptable non-toxic liquid vehicle to yield an injectable vaccine. For example, vaccination of Syrian hamsters with a single dose of a suspension of about 50–100 $\mu$g (dry weight) of the inactivated spirochetes in normal saline provided 86–100% protection against infection due to a subsequent *B. burgdorferi* challenge.

DETAILED DESCRIPTION OF THE INVENTION

The immunogenic whole cell isolate which is employed as the active component of the present vaccines consists essentially of inactivated *Borrelia burgdorferi* spirochetes. These spirochetes can be isolated from infected hosts or vectors of Lyme borreliosis. For example, the spirochetes have been isolated from cerebrospinal fluid, blood or skin lesions of human patients afflicted with Lyme disease as well as from *I. dammini* ticks, as disclosed by A. C. Steele et al., *The New England Journal of Medicine*, 308, 733 (1983), the disclosure of which is incorporated by reference herein. The spirochetes can be maintained in infected laboratory animals, such as hamsters, or in suitable nutrient media. The immunogenic spirochetes can be isolated from the spleens of the infected animals and media-cultured. The spirochetes can then be separated from the medium by centrifugation, filtration and the like. The cellular isolate can be dried by lyophilization of an aqueous suspension thereof to yield deactivated whole cells.

The dried whole cells may then be adjusted to an appropriate concentration, optionally combined with a suitable vaccine adjuvant, and packaged for use. Suitable adjuvants include but are not limited to: surfactants, e.g., hexadecylamine, octadecylamine, lysolecithin, dimethyldioctadecylammonium bromide, N,N-dioctadecyl-N'-N-bis(2-hydroxyethyl-propane diamine), methoxyhexadecylglycerol, and pluronic polyols; polyanions, e.g., pyran, dextran sulfate, poly IC, polyacrylic acid, carbopol; peptides, e.g., muramyl dipeptide, dimethylglycine, tuftsin; oil emulsions; and alum. Finally, the immunogenic product may be incorporated into liposomes for use in a vaccine formulation, or may be conjugated to polysaccharides or other polymers.

The absolute weight of the deactivated whole cells included in a given unit dosage form of vaccine can vary widely, and depends upon factors such as the age, weight and physical condition of the subject considered for vaccination. Such factors can be readily determined by the clinician or veterinarian employing animal models or other test systems which are well known to the art. A unit dose of the vaccine is preferably administered parenterally, e.g., by subcutaneous or by intramuscular injection.

The invention will be further described by reference to the following detailed examples.

EXAMPLE I

Vaccine Preparation and Vaccination

A. Origin and Cultivation of *Borrelia burgdorferi*

The human spinal fluid (HSF) isolate of *Borrelia burgdorferi* spirochetes was supplied by Allen Steere, Yale University, New Haven, Conn. The isolate was obtained from the spleen of an experimentally-infected Syrian hamster and has been passaged from hamster to hamster a minimum of 10 times. The spirochetes employed to infect the hanster were isolated from HSF and cultured as disclosed by A. C. Steele et al., *New Engl. J. Med.*, 308, 733 (1983), the disclosure of which is incorporated by reference herein.

The isolate was cultivated in a modified Barbour-Stoenner-Kelly (BSK) medium at 30° C. in air to a density of $1 \times 10^8$ spirochetes/ml. The modified medium was prepared by the addition of 0.15% agarose (Seakem LE; FMC Corp., Rockland, Me.) to the BSK medium. The BSK medium was prepared as disclosed by A. G. Barbour, Isolation and cultivation of Lyme disease spirochetes, in *Lyme Disease, First International Symposium*, A. C. Steele, S. E. Malawista, J. E. Craft, D. K. Fisher and M. Garcia-Blanco (eds.)., The Yale Journal of Biology and Medicine, Inc., New Haven (1984), at pages 71-75, the disclosure of which is incorporated by reference herein.

Spirochetes were harvested by centrifugation, resuspended in a small volume of distilled water and lyophilized. This cellular preparation was devoid of viable cells. Neither culture or injection of 100 µg of the cell preparation into hamsters provided evidence of viable spirochetes.

The vaccine was prepared by suspending the appropriate dry weight of cells in sterile saline containing 0.01% thimerosal. Male and female hamsters, 5-10 weeks old, were injected with a single dose of vaccine subcutaneously.

EXAMPLE II

Challenge and Isolation of *B. burgdorferi*

Thirty days or 90 days after vaccination, hamsters were challenged by the intraperitoneal injection of $1 \times 10^8$ cells of a hamster spleen isolate of *B. burgdorferi*, HSF which had not been subcultured more than three times. This challenge dose represents approximately 1000 50% infectious doses of this spirochete. The hamsters were sacrificed and the kidneys and spleens cultured at 14 days post-challenge. Individual hamster organs were placed in 6 ml BSK medium and homogenized with a Stomacher Lab-Blender (Tekmar Co., Cincinnati, Ohio). The larger tissue debris was allowed to settle and duplicate 1:10 dilutions of the supernatant were made in the isolation medium (BSK medium plus 0.15 percent agarose). Cultures were examined for spirochetes after three weeks of incubation at 30° C. An animal was considered culture-positive if spirochetes could be isolated from one or more organs. The results of these experiments are summarized in Table I (below).

TABLE I

Active Immunization of Hamsters Against Experimental Infection with *Borrelia burgdorferi*

| Vaccine preparation (µg dry weight) | Number cultures-negative animals: Total number of animals Experiment Number | | |
|---|---|---|---|
| | 1[a] | 2[a] | 3[b] |
| 0 (saline control) | 0/20 | 0/15 | 1/15 |
| 10 | 0/10 (0)[c] | — | — |
| 25 | — | 13/19 (68) | 1/20 (5) |
| 50 | 12/14 (86) | 20/20 (100) | 8/20 (40) |
| 100 | 14/14 (100) | 18/20 (90) | 5/20 (25) |

[a]Animals challenged 30 days post-vaccination
[b]Animals challenged 90 days post-vaccination
[c]Number in brackets indicates percent protection to challenge One-hundred percent of the control hamsters receiving saline injections were culture-positive following challenge. The smallest dose of vaccine tested, 10 µg, did not provide protection to the thirty-day challenge. Increasing the amount of vaccine to 25 µg elicited a protective response to the thirty-day challenge in 68% of the vaccinates. Eighty-six percent to 100% of the hamsters receiving 50 µg of the cell preparation were protected from the thirty-day challenge. A further increase in the amount of vaccine to 100 µg provided a degree of protection similar to that achieved with 50 µg.

The protective response induced in hamsters receiving a single dose of vaccine decreased significantly by 90 days post-vaccination. Protection decreased to 5%, 50% and 25% for the 25 µg, 50 µg and 100 µg doses of vaccine, respectively. Hamster blood was not examined for anti-*B. burgdorferi* antibodies during the course of the vaccination studies because of the possibility of compromising the results of the experiments. Blood was obtained by cardiac puncture from a group of five hamsters vaccinated with 100 µg of the cell preparation. The indirect immunofluorescent antibody titer of the pooled sera was 1:8 at day 0, 1:128 at day 14, 1:256 at day 30 and 1:64 at 90 days post-vaccination.

Although the duration of immunity elicited by a single vaccination was relatively short-lived in the hamster, the data summarized in Table I indicates the efficacy of vaccination as a method for the prevention of Lyme disease. A further study of the passive immunization of hamsters against infection with *B. burgdorferi* indicated that isolates from the north-central United States and northeastern United States produced mutually protective antibodies in the rabbit. These results suggest that a monovalent vaccine should be effective in these two disparate geographical areas.

EXAMPLE III

Vaccination of Dogs

Dogs were injected intramuscularly with vaccine prepared in accord with Example I. The dogs received two injections of the vaccine (200 µg whole cells in 1.0 ml saline containing 6% alum) at two-week intervals. The antibody levels were determined by indirect immunofluorescence assay (IFA) and are summarized on Table II, below.

TABLE II

| | Vaccination of Dogs | | | | |
|---|---|---|---|---|---|
| | Dog Number | | | | |
| Antibody Titer | 1 | 2 | 3 | 4 | 5 |
| Prevaccination titer | <1:5 | <1:5 | <1:5 | <1:5 | <1:5 |

TABLE II-continued

| | Vaccination of Dogs | | | | |
|---|---|---|---|---|---|
| | Dog Number | | | | |
| Antibody Titer | 1 | 2 | 3 | 4 | 5 |
| Two weeks after first vaccination and at time of second vaccination | 1:80 | 1:10 | 1:160 | 1:160 | 1:80 |
| Two weeks after second vaccination | 1:320 | 1:320 | 1:640 | 1:320 | 1:160 |

The data summarized on Table II indicate that a second injection of the present vaccine is capable of boosting the levels of serum antibodies in the dog.

Thus, the use of a plurality of vaccinations is expected to increase the duration of immunity conferred and it is expected that a vaccine comprising inactivated *B. burgdorferi* spirochetes will be effective to actively immunize susceptible mammals against Lyme borreliosis.

Furthermore, it is expected that the efficacy of vaccines based on *B. burgdorferi* spirochetes will be increased by employing immunogenic fractions derived therefrom by methods which are known to the art. For example, the borrelial outer envelope which surrounds the protoplasmic cylinder of spirochetes can be readily extracted [E. C. Klaviter et al., *Acta. Trop.*, 36, 123 (1979)]. This fraction may provide immunogens which impart an equal or greater resistance to Lyme borreliosis infection when employed as the active component of vaccines prepared in accord with the present invention.

The invention has been described with reference to various specific and preferred embodiments and techniques. However, it should be understood that many variations and modifications may be made while remaining within the spirit and scope of the invention.

What is claimed is:

1. A vaccine comprising an immunogenic amount of inactivated *Borrelia burgdorferi* spirochetes dispersed in a physiologically-acceptable, non-toxic liquid vehicle, which amount is effective to immunize a susceptible mammal against Lyme borreliosis.

2. The vaccine of claim 1 wherein the inactivated *Borrelia burgdorferi* spirochetes are obtained by culturing immunogenic *Borrelia burgdorferi* spirochetes, separating the spirochetes from the culture medium by centrifugation and lyophilizing the separated spirochetes.

3. The vaccine of claim 2 wherein the immunogenic *Borrelia burgdorferi* spirochetes are derived from spleens of hamsters infected with *Borrelia burgdorferi* spirochetes derived from human spinal fluid.

4. A method for the immunization of a mammal against Lyme borreliosis comprising administering to said mammal an effective amount of the vaccine of claim 1.

5. The method of claim 4 wherein the vaccine is administered by injection.

6. The method of claim 5 wherein a plurality of injections of the vaccine are administered.

* * * * *

UNITED STATES PATENT AND TRADEMARK OFFICE
CERTIFICATE OF CORRECTION

PATENT NO. : 4,721,617

DATED : January 26, 1988

INVENTOR(S) : Russell C. Johnson

It is certified that error appears in the above-identified patent and that said Letters Patent is hereby corrected as shown below:

At Col. 4, line 31, for "50% and 25%" read --40% and 25%--.

Signed and Sealed this

Twenty-eighth Day of June, 1988

Attest:

DONALD J. QUIGG

Attesting Officer

Commissioner of Patents and Trademarks